United States Patent [19]
Dahlke

[11] Patent Number: 5,991,355
[45] Date of Patent: Nov. 23, 1999

[54] DEVICE FOR COUNTING THE NUMBER OF USES OF A SENSOR

[75] Inventor: Mikael Dahlke, Trangsund, Sweden

[73] Assignee: Siemens Elema AB, Solna, Sweden

[21] Appl. No.: 09/098,495

[22] Filed: Jun. 17, 1998

[51] Int. Cl.[6] ................................................. G07C 3/00
[52] U.S. Cl. ............................. 377/15; 377/16; 604/52; 604/53
[58] Field of Search .................... 604/52, 53; 377/15, 377/16

[56] References Cited

U.S. PATENT DOCUMENTS

| | | | |
|---|---|---|---|
| 5,313,935 | 5/1994 | Kortenbach et al. | 128/4 |
| 5,359,993 | 11/1994 | Slater et al. | 128/4 |
| 5,383,875 | 1/1995 | Jackson et al. | 606/1 |
| 5,400,267 | 3/1995 | Denen et al. | 364/552 |

Primary Examiner—Margaret Rose Wambach
Attorney, Agent, or Firm—Hill & Simpson

[57] ABSTRACT

A device for counting the number of usage cycles of a sensor, for intracorporeal electrophysiological measurement and/or therapy, has a counting unit, connected to the sensor, containing a specific identification code for the sensor, and a detection unit which detects the sensor's connection/disconnection to/from external measurement and therapy equipment. The detection unit causes a sensing unit to read a sensor identification code in the counting unit whenever the sensor is connected so as to determine, from information about sensor usage stored in a main computer, whether conditions for a new usage cycle have been met and, if so, increments the counter's contents by one usage cycle.

9 Claims, 1 Drawing Sheet

DEVICE FOR COUNTING THE NUMBER OF USES OF A SENSOR

BACKGROUND OF THE INVENTION

1. Field of the Invention

The present invention relates to a device for counting the number of uses of a sensor, particularly an intracorporeal medical sensor.

2. Description of the Prior Art

Devices for counting the number of usage cycles of a sensor for intracorporeal electrophysiological measurement and/or therapy are known which generally include a counting unit, connected to the sensor, containing an identification code specific to the sensor, detection means arranged to detect when the sensor is connected/disconnected to/from external measurement and/or therapy equipment.

For safety reasons, sensors, requiring sterilization between each use, for intracorporeal measurement and/or therapy may only be reused a limited number of times, usually 5 to 10 times. Demands have even be made to restrict such sensors, e.g. electrode catheters, to a single use only, i.e. so that they are used as disposable items.

When sensors are reused, it is very important to keep a careful record of and to track the number of reuses in a way which is not susceptible to manipulation.

U.S. Pat. No. 5,383,874 describes a system for identifying and monitoring the use of ablation catheters. These catheters have an identification code which designates the catheter's operating characteristics. Connecting the catheter to ablation equipment causes the code to be read and compared to predefined operating criteria. The equipment supplies the catheter with ablation energy only if the code meets these criteria. A usage register is provided whose contents are incremented by one for each permissible use of the catheter to ensure that the catheter is not used too many times.

SUMMARY OF THE INVENTION

An object of the present invention is to provide an improved device for tracking the use of sensors of the type described above, such as electrode catheters, requiring sterilization between each cycle to keep the sensor from being used for too many cycles.

In a device according to the invention, a sensing unit is devised to automatically read a sensor's identity code, stored in the counting unit, every time when the sensor is connected in order to determine from information stored in a main computer whether conditions for a new usage cycle have been met and, if so, to increment the contents of the counting unit by one usage cycle in a reliable fashion which is not susceptible to manipulation. If, however, the sensor is removed from the patient to be cleaned from coagulated blood and re-introduced into the patient in the same examination, this reuse is not counted as a new usage cycle, since no new sterilization of the sensor is performed. The greatest "wear and tear" on the sensor occurs in sterilization. The present invention causes counting to be performed only when the sensor is connected to measurement and/or therapy equipment, since the counting unit requires electrical energy but not in conjunction with sterilization.

DESCRIPTION OF THE PREFERRED EMBODIMENTS

Figure 1:
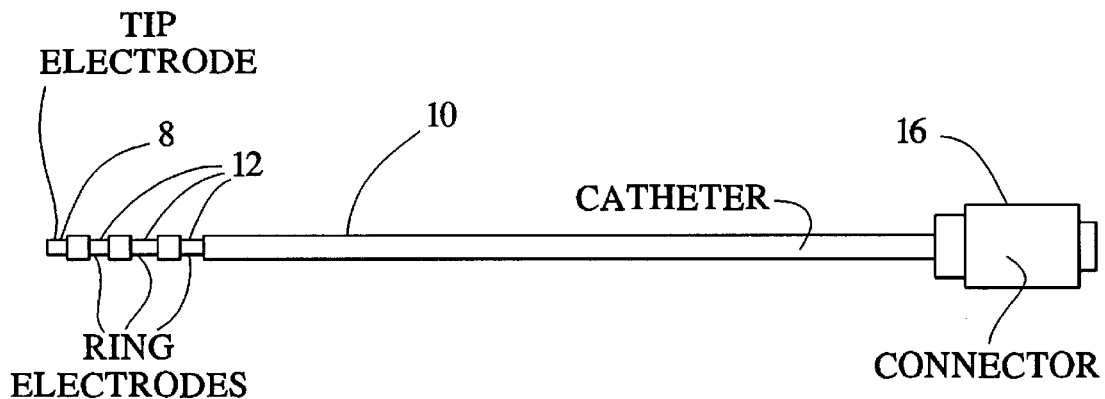
FIG. 1 shows an embodiment of a sensor in the form of an electrode catheter with a multi-pole connector for connecting the catheter.

FIG. 1 shows a 4-pole electrode catheter with a tip electrode B on the distal end and three ring electrodes 12 arranged at intervals along the catheter's opposite end section. The electrodes 8 and 12 are connected, via separate conductors inside the catheter 10, to a multi-pole connector 16.

Figure 2:
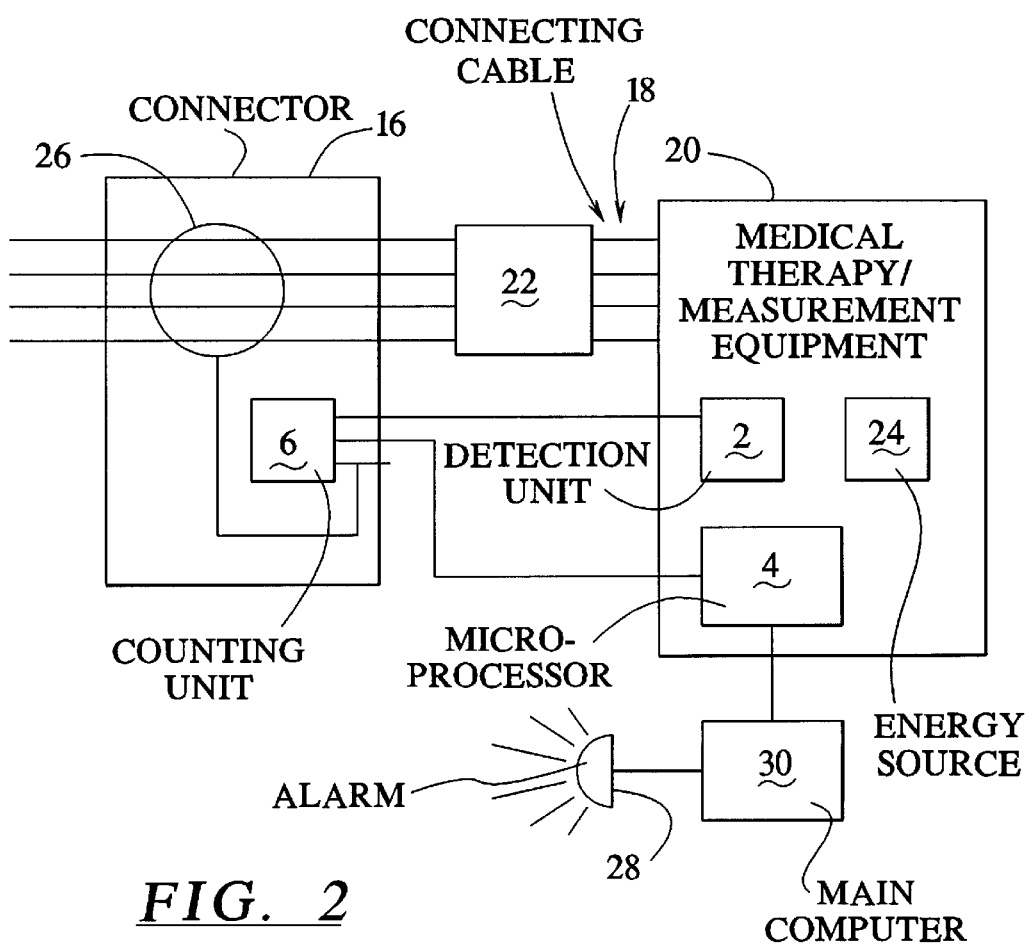
FIG. 2 is a block diagram showing an embodiment of the device according to the invention.

FIG. 2 shows the connector 16 connected to a connecting cable 18, for connecting the electrode catheter 10 to measurement and/or therapy equipment 20 located outside the patient. The equipment 20 is electrophysiological measurement and/or therapy equipment. It can be e.g. a recording apparatus, such as an ECG recorder, or a therapy apparatus in the form of an ablation generator. An amplifier 22 is appropriately arranged in this part of the setup to amplify signals picked up by the electrode catheter 10.

A programmable counting unit 6, appropriately a PROM, is mounted inside the multi-pole connector 16. Two additional pins are required, viz, one for connecting the counting unit 6 to an electrical energy source 24 and one for duplex transmission of data to a sensing unit in the form of a microprocessor 4. A ground pin is connected to the same ground as for the cable sleeve, as indicated at 26.

The counting unit 6 can be realized as a DS2434 integrated circuit available from Dallas Semiconductor. It has e.g. a duplex data protocol suitable for connecting the counting unit 6 to the microprocessor 4.

A detection unit 2 is connected between the counting unit 6 and the energy source 24 for detecting connection/disconnection of the electrode catheter to/from the measurement and/or therapy equipment 20. When the connector 16 is connected to the measurement and/or therapy equipment 20, the counting unit 6 is accordingly connected, via one of its pins, to the energy source 24. Connection of the connector 16 is therefore detected when the detection unit 2 senses current being sent to the counting unit 6.

The detection unit 2, the energy source 24 and the microprocessor 4 are suitably arranged in the measurement and/or therapy equipment 20.

An identification code for the electrode catheter 10 employed is stored in the connector 16, suitably as a bit pattern in a PROM. Alternatively, the code can be stored in the contact part of an adapter cable. This identification code can be a code, designating the manufacturer, the type of catheter and serial number, stored in a ROM in the counting unit 6.

When the electrode catheter is connected, the microprocessor 4 senses the identification code in the counting unit 6 via the duplex data protocol. The read identification code is sent to a main computer 30 in which information on the previous use of the catheter 10 is stored. If conditions for registering a new usage cycle are met, i.e. a new patient or a new examination, preceded by sterilization of the catheter 10, is involved, the counting unit 6 is incremented by one step. Thus, the counting unit 6 appropriately has a read-write memory whose contents are incremented by one when conditions for a new usage cycle are met. The physician sometimes has reason to remove the catheter from the patient in order to clean e.g. coagulated blood off its tip, and then reinsert it into the patient. This operation is not registered as a new usage cycle.

An optical and/or acoustic alarm 28 can be connected to the main computer 30 for indicating when the number of usage cycles reaches a maximum permissible upper limit.

One embodiment, using one sensor in the form of a 4-pole electrode catheter, was described above. Measurement and/or therapy equipment can naturally be devised for a much larger number of poles to permit the use of different electrode catheter configurations. Other types of sensors can also be used, such as sensors for measuring intracorporeal temperature and pressure and for measuring the oxygen content of blood in the heart.

As an alternative to the embodiment described above, the identification code stored in the PROM in the counting unit 6 can be the address of a table of sensor identification information stored in measurement and/or therapy equipment 20, this address being readable by the microprocessor 4, whereupon present identification information is read from the table and sent to the main computer 30 for determination of whether a new usage cycle is present.

Although modifications and changes may be suggested by those skilled in the art, it is the intention of the inventor to embody within the patent warranted hereon all changes and modifications as reasonably and properly come within the scope of his contribution to the art.

I claim as my invention:

1. A device for counting the number of usage cycles of a sensor for intracorporeal use, comprising:

a sensor adapted for intracorporeal use in a subject, said sensor requiring electrical energy for operation thereof;

a counting unit connected to said sensor and containing an identification code unique to said sensor;

extracorporeal equipment to which said sensor is connectable for supplying electrical energy to said sensor;

detection means for detecting each connection of said sensor to said extracorporeal equipment and disconnection of said sensor from said extracorporeal equipment and for generating a detection signal upon each connection and disconnection;

a computer containing stored information identifying previous usage of said sensor; and sensing means connected to said detection means and to said computer for, upon receipt of said detection signal, determining from said information stored in said main computer whether conditions for a new usage cycle exist and, if so, for incrementing said counting unit by one usage cycle.

2. A device as claimed in claim 1 wherein said extracorporeal equipment comprises an electrical energy source, and wherein said counting unit is connected to said electrical energy source when said sensor is connected to said extracorporeal equipment, said detection means comprising means for identifying connection of said sensor to said extracorporeal equipment as equal to connection of the counting unit to said energy source.

3. A device as claimed in claim 1 wherein said counting unit contains a read-write memory, and wherein said sensing means comprises means for incrementing contents of said read-write memory by one when said conditions for a new usage cycle exist.

4. A device as claimed in claim 1 wherein said sensor has a sensor connector for connection to said extracorporeal equipment, and wherein said counting unit is disposed in said sensor connector.

5. A device as claimed in claim 4 wherein said counting unit is disposed in said sensor connector so as to be connected to an electrical energy source whenever said sensor is connected to said external equipment.

6. A device as claimed in claim 1 wherein said counting unit has a ROM containing an identification code unique to said sensor designating a manufacturer, a sensor type and a serial number.

7. A device as claimed in claim 1 further comprising alarm means connected to said main computer for identifying when a number of usage cycles reaches a permissible maximum upper limit.

8. A device as claimed in claim 1 wherein said sensing means comprises a microprocessor.

9. A device as claimed in claim 8 wherein said microprocessor is connected to said counting unit via a duplex data protocol arrangement.

* * * * *